United States Patent [19]

Wolk

[11] Patent Number: 5,704,784
[45] Date of Patent: Jan. 6, 1998

[54] QUICK-RELEASE MECHANISM FOR ORTHODONTIC HEADGEAR ASSEMBLY

[76] Inventor: Roger S. Wolk, 28 Malibu Colony, Malibu, Calif. 90265

[21] Appl. No.: 553,076

[22] Filed: Nov. 3, 1995

[51] Int. Cl.⁶ .................................................. A61C 7/00
[52] U.S. Cl. ............................................................ 433/5
[58] Field of Search .................................................. 433/5

[56] References Cited

U.S. PATENT DOCUMENTS

| | | | |
|---|---|---|---|
| 4,215,983 | 8/1980 | Frazier | 433/5 |
| 4,226,589 | 10/1980 | Klein | 433/5 |
| 4,253,691 | 3/1981 | Hickham | 433/5 |
| 4,264,302 | 4/1981 | Wolk et al. | 433/5 |
| 4,872,836 | 10/1989 | Grove | 433/5 |

Primary Examiner—Cary E. O'Connor
Attorney, Agent, or Firm—Thomas I. Rozsa; Tony D. Chen

[57] ABSTRACT

A quick-release mechanism for an orthodontic headgear assembly, which has a bracket integrally formed with a traction force device and a connecting structure attached to ends of a neckstrap or headstrap. The bracket has two opposite horizontal parallel arms that extend rearwardly and a vertical rod integrally attached between the two opposite parallel arms. The connecting structure is snapped onto the vertical rod for retaining the traction force device and the neckstrap in position. The quick-release mechanism is disconnected by vertically pulling the connecting structure and the bracket apart from each other at a predetermined force, thereby releasing the connecting structure from the bracket.

5 Claims, 2 Drawing Sheets

5,704,784

QUICK-RELEASE MECHANISM FOR ORTHODONTIC HEADGEAR ASSEMBLY

BACKGROUND OF THE INVENTION

1. Field of the Invention

The present invention relates to the field of orthodontic appliances. More particularly, the present invention relates to the field of quick-release mechanisms for an orthodontic headgear assembly.

2. Description of the Prior Art

It is common to use an orthodontic headgear assembly to apply a steady continuous force to a patient's teeth for the purpose of assisting in obtaining or maintaining of proper occlusion. The orthodontic headgear assembly includes a face bow and a neckstrap or headstrap, or the like. The facebow includes an inner bow which seats in tubes, or other suitable devices, mounted on bands which have been attached to the patient's teeth, and an outer bow which is attached to the inner bow, and which extends around the opposite sides of the patient's face. Tension is generally applied by tension-applying mechanisms which are attached to the ends of the neckstrap. Force cables or straps, or the like extend out from the tension-applying mechanisms and hooked to the outer bow in the facebow.

In the past, it has been a common design to provide a release mechanism in conjunction with the orthodontic headgear assembly. The function for the release mechanism is that if the tension-applying mechanism is disengaged from the neckstrap, the facebow will physically break apart, thereby preventing snap-back and injury to the wearer. In addition, the orthodontic headgear assembly is worn mostly in the evening and sleeping hours. The disadvantage with prior art release mechanisms is that they have not been designed to facilitate ease of removal and reinstallation and the release mechanism will disengage accidentally because the release force is unreliable.

The following two (2) prior art patents were uncovered in the pertinent field of the present invention:

1. U.S. Pat. No. 4,226,589 issued to Klein on Oct. 7, 1980 for "Orthodontic Headgear Release" (hereafter "the Klein Patent"); and 2. U.S. Pat. No. 4,872,836 issued to Grove on Oct. 10, 1989 for "Releasable Extraoral Orthodontic Appliance" (hereafter "The Groove Patent").

The Klein Patent discloses an orthodontic headgear release assembly. It comprises a safety-release tension-applying mechanism for use between an orthodontic facebow and a headstrap. The mechanism comprises a pair of releaseably interengageable parts. One part includes a pair of spaced opposed relatively movable fingers which act as an infinitely changeable tension-producing gripper, and the other part includes a portion shaped to be releasably gripped by the gripper. As tension is increased and transmitted through the mechanism, the two parts tend to shift apart from one another, with gradual spreading of the fingers of the gripper. The fingers function as active tension-applying elements in an overall assembly including a headstrap and an orthodontic facebow. The parts in the mechanism continue to move apart with increased tension, where the two parts in the mechanism are automatically and smoothly released from each other.

The Grove Patent discloses a releasable extraoral orthodontic appliance. It comprises an encircling assembly located about the head of the wearer. The encircling assembly comprises a single release mechanism incorporated at the nape of the wearer and separates the encircling assembly upon the encircling assembly incurring an unusual force tending to enlarge the enclosed area of the encircling assembly.

The inventor of the present invention is one of the patentees of U.S. Pat. No. 4,264,302 issued to Wolk et al. on Apr.28, 1981 for "Orthodontic Appliance" (hereafter "the '302 Patent"), which discloses an extraoral orthodontic appliance. It comprises a harness for mounting on the head and/or neck of a patient and connected to a conventional corrective tractive apparatus, such as J-hooks, a facebow or a chin cup by traction force devices mounted on each side of the harness. The traction force devices apply a substantially constant predetermined force to the corrective tractive apparatus at all times during which the patient wears the orthodontic appliance including when the head of the patient is moved either up and down or from side to side and as movement of the dental-facial structure occurs. The traction force devices are readily adjustable with respect to changing the force levels established by the devices.

The inventor of the present invention has made a significant improvement on the '302 Patent, in which quick-release mechanisms are provided with the orthodontic headgear assembly, where if either one of the traction force devices malfunction, it can be individually replaced with another traction force device without discarding the entire neckstrap and the other traction force device, thereby providing a very cost effective design and construction of an orthodontic headgear assembly.

SUMMARY OF THE INVENTION

The present invention is a unique quick-release mechanism for an orthodontic headgear assembly. The present invention quick-release mechanism is incorporated with a traction force device which is disclosed in the '302 Patent. The quick-release mechanism comprises a bracket means integrally formed with the traction force device and a connecting means attached to ends of a neckstrap or headstrap. The bracket means has two opposite parallel arms that extend rearwardly from the traction force device and a vertical rod integrally attached between the two parallel arms. The connecting means is snapped onto the vertical rod for retaining the traction force device and the neckstrap in position. The quick-release mechanism can be disconnected by vertically pulling the bracket means and the connecting means apart from each other at a predetermined force, thereby releasing the connecting means from the bracket means.

It has been discovered, according to the present invention, that by providing an orthodontic headgear assembly with quick-release mechanisms, it will provide a way to release the neckstrap from the traction force devices.

It is therefore an object of the present invention to provide an orthodontic headgear assembly which comprises quick-release mechanisms for releasing the neckstrap from the traction force devices, and thereby facilitate the removal of the orthodontic headgear assembly.

It is an additional object of the present invention to provide an orthodontic headgear assembly which comprises quick-release mechanisms so that if one of the two traction force devices malfunction, only one needs to be replaced instead of the entire neckstrap and the other traction force device.

It is a further object of the present invention to provide a quick-release mechanism which, while capable of releasing the connection between the traction force device and the neckstrap, is also capable of transmitting the desired normal range of orthodontic tension without releasing the connection.

In the preferred embodiment of the present invention, the quick-release mechanism is incorporated with a traction force device.

In an alternative embodiment of the present invention, the quick-release mechanism is incorporated with other prior art tension-applying mechanisms.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
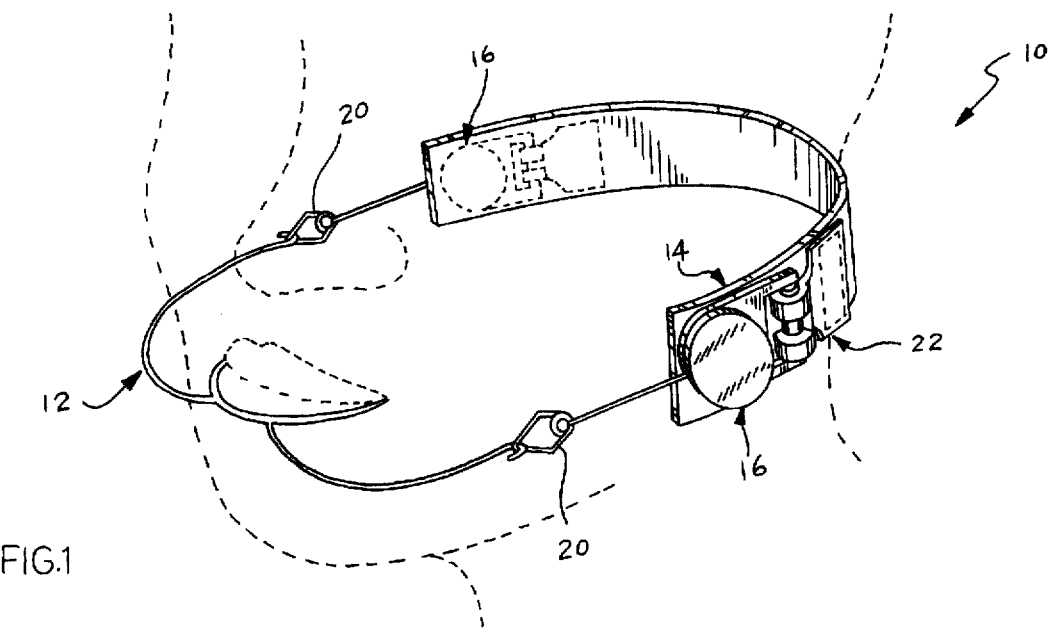
FIG. 1 is a simplified perspective view of the present invention, showing a patient wearing an orthodontic headgear assembly which employs a pair of quick-release mechanisms incorporated with a pair of traction force devices.

Referring to FIG. 1, there is shown at 10 a perspective view of an orthodontic headgear assembly properly positioned for use on a patient's head. The orthodontic headgear assembly 10 includes a conventional face bow 12 whose outer ends extend along the opposite sides of the patient's face, and a conventional flexible nonelastic or elastic neckstrap or harness 14 for fastening on the head and/or neck of the patient. There are two identical force traction devices 16 that are provided and located at opposite ends of the harness 14. The traction force devices 16 are interconnected to the opposite outer ends of the facebow 12 with end loops 20. Up to this point of the description, the construction of the force traction devices 16 are essentially conventional and disclosed in the '302 Patent, and the description thereof will not be described, and only the improvement of the present invention will be described.

Figure 2:
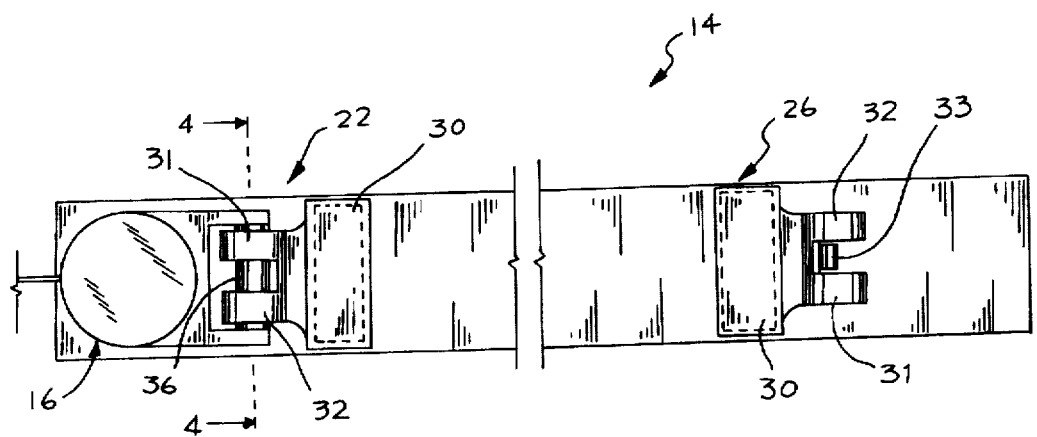
FIG. 2 is an enlarged side elevational view of the present invention, showing the quick-release mechanisms attached to ends of the neckstrap and one of the traction force devices interconnected to one of the quick-release mechanisms.
Figure 3:
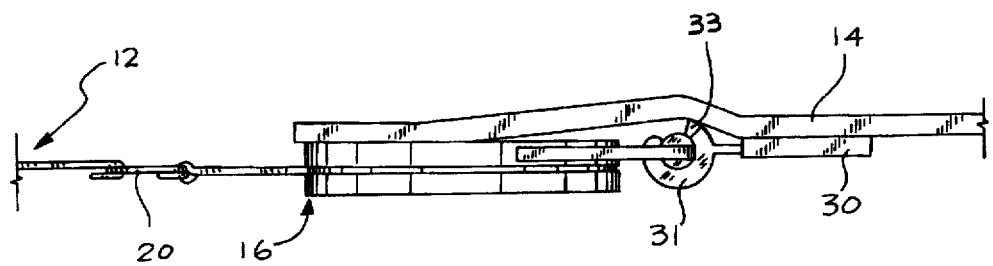
FIG. 3 is a top plan view of the present invention taken from FIG. 2.

Referring to FIGS. 2 and 3, there is shown at 14 the neckstrap, which shows the improvement of the present invention. The improvement of the present invention is a quick-release mechanism 22 incorporated with the orthodontic headgear assembly 10. Each of the quick-release mechanisms 22 are substantially identical, and to the extent they are, only one will be described in detail. The quick-release mechanism 22 comprises a connecting member 26 and a bracket member 28 (see FIG. 5). The connecting member 26 has a generally rectangular shaped plate 30 which is attached to an adjacent end of the neckstrap 14 by stitching means or other suitable means and leaves a space for the traction force device 16 to be located thereon. Three spaced apart gripping hooks or fingers 31, 32 and 33 are provided with the connecting member 26 and are integrally formed with and extend away from the plate 30 and toward the adjacent end of the neckstrap 14. The two upper gripping hooks 31 and 32 are alternatively offset from the lower gripping hook 33 (see FIG. 4).

Figure 5:
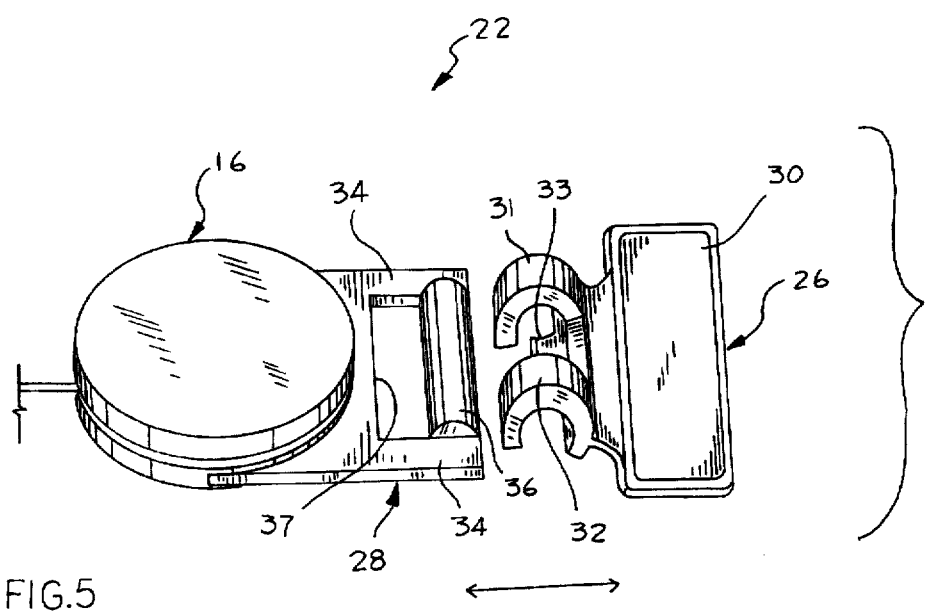
FIG. 5 is an enlarged perspective view of the present invention quick-release mechanism, showing how the quick-release mechanism is disconnected.

Referring to FIG. 5, there is depicted the present invention quick-release mechanism 22. The bracket member 28 is integrally formed with the traction force device 16. The bracket member 28 has two spaced apart horizontal parallel arms 34 which are integrally formed at the rear of the traction force device 16. A vertical rod 36 is integrally attached between the two parallel arms 34 such that there is a space or gap 37 from the vertical rod 36 to the rear of the traction force device 16.

The three gripping hooks 31, 32 and 33 are snapped onto the vertical rod 36 as shown in FIGS. 2 and 3 such that the traction force device 16 is positioned at the end of the neckstrap 14 as shown in FIG. 2. In the prior art, the traction force device 16 is directly attached to the neckstrap 14 as disclosed in the '302 Patent. The improvement in the present invention is that the traction force device 16 is not directly attached to the neckstrap 14 but the present invention quick-release mechanism 22 is attached directly to the traction force device 16 on one side, and to the neckstrap 14 on the other side.

The quick-release mechanism 22 can be released from the vertical rod 36 by pulling the bracket member 28 and the connecting member 26 apart from each other at a predetermined force, where the quick-release mechanism 22 facilitates the release of the harness 14 from the traction force devices 16, and thereby facilitates the removal of the orthodontic headgear assembly 10.

Figure 4:
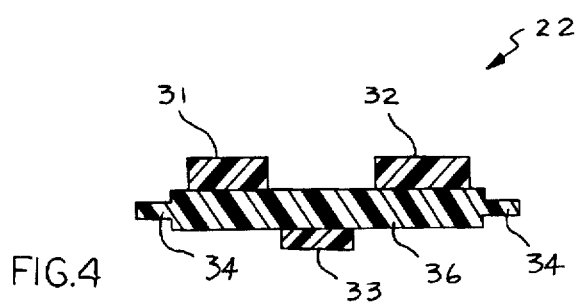
FIG. 4 is a cross-sectional view taken along line 4—4 of FIG. 2.

Referring to FIG. 4, there is shown a cross-sectional view of the present invention quick-release mechanism 22. The quick-release mechanism 22 can be made from several materials. The manufacturing process which could accommodate the construction of the quick-release mechanism can be injection, thermoform, etc. or other molding process. By way of example, the quick-release mechanism 22 can be made of plastic material, which is similar to the material that the traction force device 16 is made. The present invention conforms to conventional forms of manufacture, and is of simple construction and is easy to use.

Figure 6:
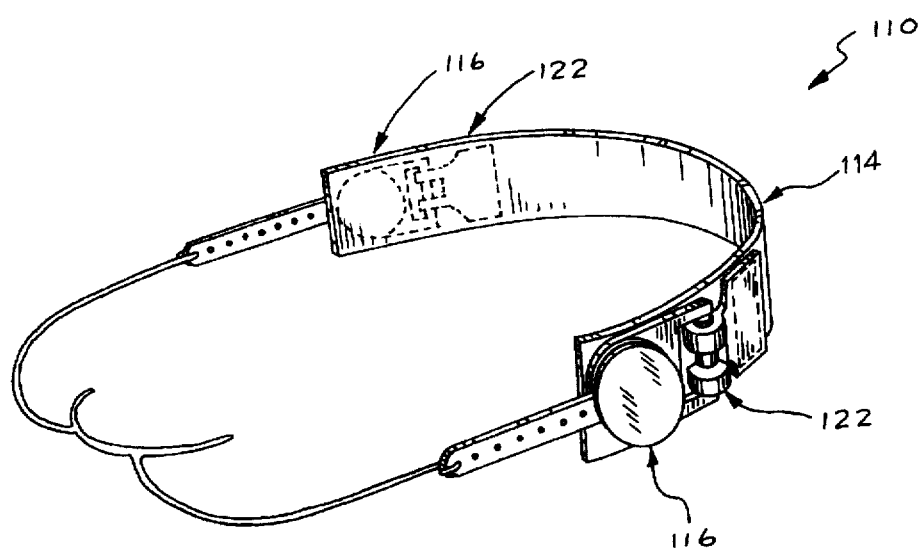
FIG. 6 is a simplified perspective view of the present invention quick-release mechanism incorporated with a prior art tension-applying mechanism.

Referring to FIG. 6, there is shown at 110 a perspective view of an orthodontic headgear assembly. The alternative embodiment of the present invention, the quick-release mechanism 122 is incorporated with conventional tension-applying mechanisms. All of the parts of the quick-release mechanism 122 is the same as previously described above, and their reference numbers are corresponding with 100 added to each number. In this embodiment, the traction force devices 16 (shown in the previous figures) are substituted with conventional tension-applying mechanisms 116. The quick-release mechanism 122 is incorporated with the tension-applying mechanisms 116 and the harness 114.

It will be appreciated that the quick-release mechanism may be incorporated to any conventional tension-applying mechanism used in orthodontic appliances not illustrated.

One of the unique features of the present invention quick-release mechanism is that if either one of the two traction force devices malfunction, only one needs to be replaced instead of the entire neckstrap assembly which includes the two opposite traction force devices. Another feature of the quick-release mechanism is that it provides a constant release force, thereby providing a reliable mechanism.

The quick release device of the present invention can be made of any material; for example plastic.

Defined in detail, the present invention is a quick-release mechanism for an orthodontic headgear assembly including a facebow, a harness for mounting on the head and/or neck of a patient and a traction force device attached to the facebow for applying a traction force, where the quick-release mechanism is operatively interposed between the traction force device and an adjacent end of the harness, the quick-release mechanism comprising: (a) a connecting member having a plate and a multiplicity of spaced apart gripping hooks integrally formed with and extending away from the plate, the plate attached to the adjacent end of the harness, the multiplicity of spaced apart gripping hooks all being alternatively offset from each other; and (b) a bracket member mounted to the traction force device and having two spaced apart horizontal parallel arms protruding from the traction force device and a vertical rod integrally attached between the two parallel arms such that said multiplicity of spaced apart gripping hooks of said connecting member are engageably snapped onto the vertical rod, and can be released from the vertical rod by pulling the bracket member and said connecting member apart from each other at a predetermined force; (c) whereby said quick-release mechanism facilitates the release of the harness from the traction force device, and thereby facilitates the removal of the orthodontic headgear assembly.

Defined broadly, the present invention is a quick-release mechanism for operative interposition between an end of a traction force device which applies tension for an orthodontic treatment and an adjacent end of a harness for mounting on the head and/or neck of a patient, the release mechanism comprising: (a) a first member having a plate and at least two hooks integrally formed with and extending away from the plate, the plate attached to the adjacent end of the harness; and (b) a second member mounted to the traction force device and having two parallel arms protruding from the traction force device and a rod integrally attached between the two parallel arms such that said at least two hooks of said first means are engageably attached to the rod, and can be released from the rod by pulling said first member and the second member apart from each other at a predetermined force; (c) whereby said release mechanism facilitates the release of the harness from the traction force device for applying tension.

Defined more broadly, the present invention is a quick-release mechanism for operative interposition between an end of a tension device which applies a tension for an orthodontic treatment and an adjacent end of a harness which is fastened on the head and/or neck of a patient, the release mechanism comprising: (a) a first member having a plate and at least one hook integrally formed with and extending away from the plate, the plate attached to the adjacent end of the harness; and (b) a second member mounted to the tension device and having an opening for receiving said at least one hook of said first means such that said at least one hook is secured therein, and can be released from the opening by pulling said first member and the second member apart from each other; (c) whereby said quick-release mechanism facilitates the release of the harness from the tension device.

Defined even more broadly, the present invention is a release mechanism for operative interposition between an end of a means for applying tension for an orthodontic treatment and an adjacent end of a harness which is fastened on the head and/or neck of a patient, the release mechanism comprising: (a) a first means attached to the adjacent end of the harness and having at least one protruding finger; and (b) a second means attached to the means for applying tension and having an opening for receiving said at least one protruding finger of said first means such that said at least one protruding finger is secured therein, and can be released from the opening by separating said first means from the second means; (c) whereby said release mechanism facilitates the release of the harness from the means for applying tension.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A quick-release mechanism for an orthodontic headgear assembly including a facebow, a harness for mounting on the head and/or neck of a patient and a traction force device attached to the facebow for applying a traction force, where the quick-release mechanism is operatively interposed between the traction force device and an adjacent end of the harness, the quick-release mechanism comprising:

a. a connecting member having a plate and a multiplicity of spaced apart gripping hooks integrally formed with and extending away from the plate, the plate for attachment to the adjacent end of the harness, the multiplicity of spaced apart gripping hooks all being alternatively offset from each other; and b. a bracket member for adapting to the traction force device and having two spaced apart horizontal parallel arms and a vertical rod integrally attached between the two parallel arms such that said multiplicity of spaced apart gripping hooks of said connecting member are engageably snapped onto the vertical rod, and can be released from the vertical rod by pulling the bracket member and said connecting member apart from each other at a predetermined force;

c. whereby said quick-release mechanism is used for facilitating the release of the harness from the traction force device, and thereby facilitates the removal of the orthodontic headgear assembly.

2. The quick-release mechanism in accordance with claim 1 wherein said quick-release mechanism is made of plastic.

3. A quick-release mechanism for operative interposition between an end of a traction force device which applies tension for an orthodontic treatment and an adjacent end of a harness for mounting on the head and/or neck of a patient, the release mechanism comprising:

a. a first member having a plate and at least two hooks integrally formed with and extending away from the plate, the plate for attachment to the adjacent end of the harness; and b. a second member for adapting to the traction force device and having two parallel arms and a rod integrally attached between the two parallel arms such that said at least two hooks of said first member are engageably attached to the rod, and can be released from the rod by pulling said first member and the second member apart from each other at a predetermined force;

c. whereby said release mechanism is used for facilitating the release of the harness from the traction force device for applying tension.

4. The quick-release mechanism in accordance with claim 3 wherein said quick-release mechanism is made of plastic.

5. The quick-release mechanism in accordance with claim 3 wherein said at least two hooks all being alternatively offset from each other.

* * * * *